United States Patent [19]

Hashimoto et al.

[11] 4,361,437

[45] Nov. 30, 1982

[54] 3-THIOOXO-5-OXO-HEXAHYDRO-1,2,4-TRIAZINE AND ITS PRODUCTION AND USE

[75] Inventors: Shunichi Hashimoto, Sonehigashi; Hiromichi Oshio, Osaka; Masato Mizutani, Kyoto; Yuzuru Sanemitsu, Ashiya; Haruhiko Katoh, Takarazuka; Seizo Sumida, Nishinomiya; Tadashi Ooishi, Sonehigashi, all of Japan

[73] Assignee: Sumitomo Chemical Company, Limited, Osaka, Japan

[21] Appl. No.: 235,123

[22] Filed: Feb. 17, 1981

[30] Foreign Application Priority Data

Feb. 19, 1980 [JP] Japan .................................. 55-19913

[51] Int. Cl.$^3$ .................... C07D 253/06; A01N 43/64
[52] U.S. Cl. ......................................... 71/93; 544/182
[58] Field of Search .......................... 544/182; 71/93

[56] References Cited

U.S. PATENT DOCUMENTS

| | | | |
|---|---|---|---|
| 2,956,924 | 10/1960 | Ursprung | 544/182 |
| 3,412,083 | 11/1968 | Restivo | 544/182 |
| 3,544,570 | 12/1970 | Timmler et al. | 544/182 |
| 3,879,186 | 4/1975 | Wittenbrook | 260/248 AS |
| 3,879,386 | 4/1975 | Wittenbrook | 71/93 |
| 3,922,273 | 11/1975 | Deutsch | 544/182 |
| 4,057,546 | 11/1977 | Timmler et al. | 544/182 |
| 4,151,355 | 4/1979 | Merz | 544/182 |
| 4,220,767 | 9/1980 | Brown et al. | 544/182 |

FOREIGN PATENT DOCUMENTS

| | | | |
|---|---|---|---|
| 1478307 | 3/1967 | France . | |
| 2075341 | 9/1971 | France . | |
| 288889 | 2/1953 | Switzerland | 544/182 |
| 828988 | 2/1960 | United Kingdom | 544/182 |
| 1120963 | 7/1968 | United Kingdom . | |
| 1160955 | 8/1969 | United Kingdom . | |

OTHER PUBLICATIONS

Gante et al, Berichte Der Deutschen Chemischen Gesellschaft, vol. 97, pp. 994–1001, (1964).

*Primary Examiner*—John M. Ford
*Attorney, Agent, or Firm*—Birch, Stewart, Kolasch & Birch

[57] ABSTRACT

3-Thiooxo-5-oxo-hexahydro-1,2,4-triazine, which is useful as a herbicide and/or fungicide.

3 Claims, No Drawings

3-THIOOXO-5-OXO-HEXAHYDRO-1,2,4-TRIAZINE AND ITS PRODUCTION AND USE

The present invention relates to 3-thiooxo-5-oxo-hexahydro-1,2,4-triazine (hereinafter referred to as "triazine compound") and its production and use.

The triazine compound representable by the formula:

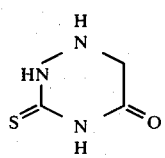

(I)

has been found to exhibit a herbicidal activity against Gramineae grasses such as barnyard grass (*Echinochloa crusgalli*), large crabgrass (*Digitaria sanguinalis*), green foxtail (*Setaria viridis*), water foxtail (*Alopecurus geniculatus*), annual bluegrass (*Poa annua*) and wild oat (*Avena fatua*) as well as broad-leaved weeds such as redroot pigweed (*Amaranthus retroflexus*), common lambsquarters (*Chenopodium album*), common chickweed (*Stellaria media*), smartweed (*Polygonum scabrum*), catchweed bedstaw (*Galium aparine*), black nightshade (*Solanum nigrum*), annual morning-glory (*Ipomoea purpurea*) and jimsonweed (*Datura stramonium*).

Advantageously, the triazine compound (I) produces a strong herbicidal potency upon application to farmland by soil treatment prior to the germination of grasses and weeds or foliar treatment at the growth period of grasses and weeds without causing any harmful effect on various crop plants (e.g. rice plant, wheat, corn, cotton, soybean, sugarbeet, peanut, sunflower) and vegetables (e.g. lettuce, tomato). In the soil treatment, a distinct herbicidal activity of the triazine compound (I) is seen even against the grasses and weeds of large seeds such as annual morning-glory, catchweed bedstraw and wild oat. It is characteristic that a strong herbicidal activity is produced against Gramineae weeds such as wild oat by foliar treatment. It is also characteristic that a residual effect is exerted over a long period of time. In addition, the triazine compound (I) may be applied to the paddy field so as to prevent and exterminate the paddy field annual and perennial grasses and weeds such as barnyard grass, pickerel weed (*Monochoria vaginalis*), tooth cup (*Lotara indica*), *Dopatrium junceum*, slender spikerush (*Eleocharis acicularis*) and hardstem bulrush (*Scirpus serotinus*) without any phytotoxicity to rice plants.

Accordingly, the triazine compound (I) is useful as a herbicide applicable for paddy fields and farmland. It is also useful as a herbicide to be employed for orchard, lawn, pasture, tea garden, mulberry field, rubber plantation, forest, non-agricultural land, etc. applications.

Apart from the herbicidal activity as stated above, the triazine compound (I) exerts a remarkable antifungal activity against various phyto-pathogenic fungi and is useful as an antifungal agent for prevention and control of plant diseases, for instance, caused by Fusarium oxysporum.

The triazine compound (I) is novel and can be produced by treatment of a thiosemicarbazide of the formula:

(II)

wherein R is hydrogen or lower alkyl with a base. As the base, there may be employed an alkali metal hydroxide (e.g. sodium hydroxide, potassium hydroxide), an alkali metal alkoxide (e.g. sodium methoxide, sodium ethoxide, potassium t-butoxide), etc. For the treatment, the base may be used in an amount of 2-3 mol to one mol of the thiosemicarbazide (II: R=H) or in an amount of 1-1.5 mol to one mol of the thiosemicarbazide (II: R=lower alkyl). The treatment is usually effected in a solvent such as water or a lower alkanol (e.g. methanol, ethanol), or a mixture thereof. The treatment may be carried out within a wide range of temperature from $-30°$ C. to the boiling temperature of the solvent, preferably from $-10°$ to $50°$ C. The treatment is normally accomplished in 10 minutes to 10 hours.

The starting thiosemicarbazide (II) may be synthesized as follows:

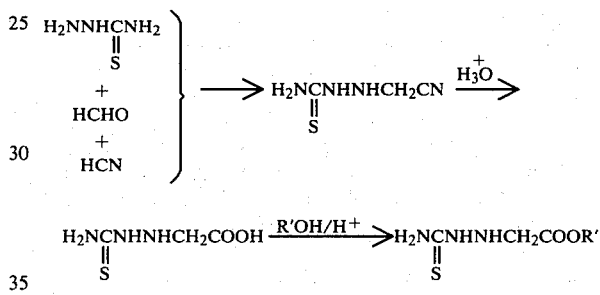

wherein R' is lower alkyl.

Namely, the reaction of thiosemicarbazide with formaldehyde and hydrogen cyanide in aqueous alcohol at $50°$ to $80°$ C. for 30 minutes to 3 hours affords 1-cyanomethylthiosemicarbazide, which is then heated in the presence of an acid for several hours to give the thiosemicarbazide (II: R=H). The thiosemicarbazide (II: R=H) can be readily converted into the thiosemicarbazide (II: R=lower alkyl) by heating with a lower alkanol in the presence of an acid.

A typical example of the production of the triazine compound (I) is set forth below together with some examples of the production of the starting thiosemicarbazide (II).

EXAMPLE 1

To a solution of metallic sodium (155 mg) in ethanol (10 ml) under ice-cooling in a nitrogen atmosphere, a solution of 4-methoxycarbonylmethylthiosemicarbazide (1.00 g) in ethanol (10 ml) was dropwise added. The resultant mixture was stirred at room temperature for 1 hour. To the reaction mixture, 0.5 N hydrochloric acid was added to make pH 5, and the solvent was evaporated by distillation under reduced pressure to give a pale yellow solid. The solid was extracted with methanol (50 ml), and the extract was filtered. The filtrate was concentrated, and the concentrated residue was purified by column chromatography on silica gel using a solvent system of chloroform and methanol (20:1 by weight) to give 3-thioxo-5-oxo-hexahydro-1,2,4-triazine (I) (0.49 g). Yield, 61.3%. M.P., 192.5° C. (decomp.) (H$_2$O).

REFERENCE EXAMPLE 1

A solution of thiosemicarbazide (18.5 g) in ethanol (40 ml), water (30 ml) and acetic acid (12 ml) was heated at 65° C. To the resultant solution, a solution of sodium cyanide (10.0 g) in water (20 ml) was dropwise added in 10 minutes, and a 35% aqueous solution of formaldehyde (17.5 g) was dropwise added thereto in 2 minutes. Stirring was continued at 80° C. for 1 hour. After cooling to room temperature, the reaction mixture was concentrated by distillation to give a dark brown solid, which was recrystallized from a mixture of methanol and water (1:1 by weight) (300 ml) to give 1-cyanomethylthiosemicarbazide (17.1 g) as dark yellow crystals. Yield, 64.8%. M.P., 161.2° C. (decomp.).

REFERENCE EXAMPLE 2

A mixture of 1-cyanomethylthiosemicarbazide (6.51 g) and conc. hydrochloric acid (52 ml) was heated with reflux for 7 hours. The reaction mixture was cooled to room temperature, and the solvent and other volatile components were evaporated by distillation under reduced pressure to give a viscous, semi-crystalline, yellow material. This material was admixed with methanol (150 ml) and conc. hydrochloric acid (2 ml), and the resultant mixture was heated with reflux for 7 hours. After cooling to room temperature, methanol was removed by distillation under reduced pressure to a half volume. The concentrated residue was admixed with water (10 ml), neutralized with a saturated aqueous solution of sodium hydroxide and concentrated by distillation under reduced pressure to give a yellow solid. The solid was extracted with methanol (100 ml) while hot and filtered. The filtrate was concentrated under reduced pressure to give a viscous, semi-crystalline, reddish brown material, which was purified by column chromatography on silica gel using chloroform to give a pale yellow solid. Recrystallization from ethanol gave 1-methoxycarbonylthiosemicarbazide (2.98 g) as white crystals. Yield, 36.5%. M.P., 142.6° C.

In the practical usage of the triazine compound (I) as a herbicide and/or fungicide, it may be applied as such or in any preparation form such as wettable powders, emulsifiable concentrate, granules, fine granules or dusts.

For production of said preparation forms, solid or liquid carriers or diluents may be used. As for the solid carrier or diluent, there may be mentioned mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be employed alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent usable for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethyleneoxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal and/or fungicidal composition of this invention, the content of the triazine compound (I) may be usually from 0.1 to 80% by weight.

The triazine compound (I) may be used together with other herbicides and/or fungicides to improve or enhance its herbicidal and/or fungicidal activity, and in some cases, to produce a synergistic effect. As the herbicides to be mixed therewith, there may be given phenoxy series herbicides such as 2,4-dichlorophenoxyacetic acid, 2-methyl-4-chlorophenoxyacetic acid and 2-methyl-4-chlorophenoxybutyric acid (including esters and salts thereof); diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine and 2-methylthio-4,6-bisisopropylamino-1,3,5-triazine; urea series herbicides such as 3-(3,4-dichlorophenyl)-1,1-dimethylurea, 3-(3,4-dichlorophenyl)-1-methoxy-1-methylurea and 1-(2,2-dimethylbenzyl)-3-p-tolylurea; carbamate series herbicides such as isopropyl-N-(3-chlorophenyl)carbamate and methyl-N-(3,4-dichlorophenyl)carbamate; thiolcarbamate series herbicides such as S-(4-chlorobenzyl)-N,N-diethylthiolcarbamate and S-ethyl-N,N-hexamethylenethiolcarbamate; acid anilide series herbicides such as 3,4-dichloropropionanilide, N-methoxymethyl-2,6-diethyl-α-chloroacetanilide, 2-chloro-2',6'-diethyl-N-butoxymethylacetanilide, 2-chloro-2',6'-diethyl-N-(n-propoxyethyl)acetanilide and N-chloroacetyl-N-(2,6-diethylphenyl)glycine ethyl ester; uracil series herbicides such as 5-bromo-3-sec-butyl-6-methyluracil and 3-cyclohexyl-5,6-trimethyleneuracil; pyridinium chloride series herbicides such as 1,1'-dimethyl-4,4-bis-pyridinium chloride; phosphorus series herbicides such as N,N-bis-(phosphonomethyl)glycine, O-ethyl-O-(2-nitro-5-methylphenyl)-N-sec-butylphosphoroamidothioate, S-(2-methyl-1-piperidylcarbonylmethyl) O,O-di-n-propyldithiophosphate and S-(2-methyl-1-piperidylcarbonylmethyl) O,O-diphenyldithiophosphate; toluidine series herbicides such as α,α,α-trifluoro-2,6-dinitro-N,N-dipropyl-p-toluidine; 5-tert-butyl-3-(2,4-dichloro-5-isopropoxyphenyl)-1,3,4-oxadiazolin-2-one; 3-isopropyl-1H-2,1,3-benzothiadiazin(4)-3H-one-2,2-dioxide; α-(β-naphthoxy)propionanilide; 4-(2,4-dichlorobenzoyl)-1,3-dimethylpyrazol-5-yl-p-toluenesulfonate and the like. But, the herbicides are not limited to these examples.

Further, the triazine compound (I) may be employed together with other fungicides so as to exert an enhanced fungicidal activity against soil-infectious fungi.

Examples of the fungicides which produce such enhanced fungicidal activity are N-trichloromethylthiotetrahydrophthalamide, pentachloronitrobenzene, 5-ethoxy-3-trichloromethyl-1,2,4-thiadiazole, 5-methyl-3-hydroxy-1,2-oxazole, 1,4-dichloro-2,5-dimethoxybenzene, O,O-dimethyl-O-(2,6-dichloro-4-methylphenyl)-phosphorothioate, dl-methyl-N-(2,6-dimethylphenyl)-N-(2-methoxyacetyl)alanylate, dl-methyl-N-(2,6-dimethylphenyl)-N-(2-furyl)ananylate, N-(3,5-dichlorophenyl)-1,2-dimethylcyclopropane-1,2-dicarbodiimide, 1,2-bis(3-methoxycarbonyl-2-thioureido)benzene, methyl-1-(butylcarbamoyl)benzimidazol-2-yl-carbamate, etc. Other fungicides as well as nematocides, insecticides, herbicides, fertilizers, etc. are also usable in combination with the triazine compound (I).

The herbicide and/or fungicide of the invention may be applied together with insecticides, nematocides, fungicides, plant growth regulators, fertilizers, etc.

When the triazine compound (I) is used as a herbicide and/or fungicide, it may be applied before or after germination of grasses or weeds in an amount within a wide range. The amount may be usually from about 2–200 grams per are, preferably from about 5–50 grams per are.

Practical embodiments of the herbicidal and/or fungicidal composition according to the invention are illustratively shown in the following examples wherein part(s) and % are by weight.

PREPARATION EXAMPLE 1

Twenty-five parts of the triazine compound (I), 2.5 parts of a dodecylbenzenesulfonate, 2.5 parts of a ligninsulfonate and 70 parts of diatomaceous earth are well mixed while being powdered to obtain a wettable powder.

PREPARATION EXAMPLE 2

Thirty parts of the triazine compound (I), 10 parts of an emulsifier ("Sorpol SM-100" manufactured by Toho Chemical Co., Ltd.) and 60 parts of xylene are well mixed to obtain an emulsifiable concentrate.

PREPARATION EXAMPLE 3

Five parts of the triazine compound (I), 1 part of white carbon, 5 parts of a ligninsulfonate and 89 parts of clay are well mixed while being powdered. The mixture is then kneaded with water, granulated and dried to obtain a granule.

PREPARATION EXAMPLE 4

Three parts of the triazine compound (I), 1 part of isopropyl phosphate, 66 parts of clay and 30 parts of talc are well mixed while being powdered to obtain a dust.

PREPARATION EXAMPLE 5

Forty parts of bentonite, 5 parts of a ligninsulfonate and 55 parts of clay are well mixed while being powdered. The mixture is then well kneaded with water, granulated and dried to obtain a granule containing no active ingredient. Ninety-five parts of the thus obtained granule are then impregnated with 5 parts of the triazine compound (I) dissolved in methanol. Subsequent removal of methanol gives a granule.

PREPARATION EXAMPLE 6

Ninety-five parts of bentonite of 16–48 mesh is impregnated with 5 parts of the triazine compound (I) dissolved in methanol. Subsequent removal of methanol gives a granule.

Some test examples which show the herbicidal activity and the fungicidal activity of the triazine compound (I) are shown in the following Examples wherein % is by weight.

TEST EXAMPLE 1

Plastic trays (35×25×10 cm) were filled with upland soil, and seeds of redroot pigweed, annual morningglory, catchweed bedstraw, wild oat and barnyard grass as well as seeds of rice plant and wheat were sowed therein. An aqueous composition prepared by diluting a wettable powder containing the triazine compound (I) with water was applied onto the entire surface of the soil in an amount of 5 liters per are by the aid of a small hand sprayer. After the application, the trays were allowed to stand in a greenhouse for 20 days. Then, the herbicidal activity and phytotoxicity were evaluated on the following criteria and indicated by numerals ranging from 0 to 5. The results are shown in Table 1.

| Numeral | Percentage of growth inhibition (%) |
|---|---|
| 0 | 0–9 |
| 1 | 10–29 |
| 2 | 30–49 |
| 3 | 50–69 |
| 4 | 70–89 |
| 5 | 90–100 |

TABLE 1

| Amount of triazine compound (I) used (g/are) | | 80 | 40 |
|---|---|---|---|
| Herbicidal activity | Annual morningglory | 5 | 5 |
| | Redroot pigweed | 5 | 5 |
| | Catchweed bedstraw | 5 | 4 |
| | Wild oat | 4 | 4 |
| | Barnyard grass | 5 | 5 |
| Phytotoxicity | Rice plant | 0 | 0 |
| | Wheat | 0 | 0 |

TEST EXAMPLE 2

Wagner's pots (1/5000 are) were each filled with upland soil, and seeds of wild oat and barnyard grass as well as seeds of rice plant and wheat were sowed therein and grown for 2 to 3 weeks in a greenhouse. A designed amount of the triazine compound (I) was sprayed to the foliage of the test plants over the top by means of a small hand sprayer. After this foliar application, the plants were grown for an additional 3 weeks in the greenhouse. The triazine compound (I) was formulated into an emulsifiable concentrate and dispersed in water for application at a spray volume of 5 liters per are with addition of a wetting agent. The herbicidal activity and phytotoxicity were examined on the same criteria as in Test Example 1. The results are shown in Table 2.

TABLE 2

| Amount of triazine compound (I) used (g/are) | | 40 | 20 |
|---|---|---|---|
| Herbicidal activity | Wild oat | 5 | 5 |
| | Barnyard grass | 5 | 4 |
| Phytotoxicity | Rice plant | 0 | 0 |
| | Wheat | 1 | 1 |

TEST EXAMPLE 3

Pots of 12 cm in diameter were filled with upland soil infected with *Fusarium oxysporum F. raphani*, and 15 seeds of raddish were sowed in each pot. A test compound formulated into an emulsifiable concentrate was diluted with water to make a 250 ppm concentration, and the dilution was poured into the pot at a rate of 20 ml per pot. Twelve days thereafter, the seedlings were cut at the ground level and browning of the trachea was observed. The disease severity was calculated according to the following equation:

$$\text{Disease severity (\%)} = \frac{\text{Number of seedlings browned at trachea}}{\text{Total number of seedlings examined}} \times 100$$

The results are shown in Table 3.

TABLE 3

| Test compound | Disease severity (%) |
| --- | --- |
| Triazine compound (I) | 0.0 |
| benzimidazole-NHCOOCH$_3$*1 with CONHC$_4$H$_9$—n | 3.2 |
| Inoculated and untreated | 78.8 |

Note:
*1 Commercially available fungicide.

What is claimed is:
1. 3-Thiooxo-5-oxo-hexahydro-1,2,4-triazine.
2. A herbicidal composition comprising a herbicidally effective amount of 3-thiooxo-5-oxo-hexahydro-1,2,4-triazine as an active ingredient and an inert carrier or diluent.
3. A method for controlling weeds and/or grasses which comprises applying a herbicidally effective amount of 3-thiooxo-5-oxo-hexahydro-1,2,4-triazine to the area where the weeds and/or grasses grow or will grow.

* * * * *